US012171613B2

(12) United States Patent
Chen et al.

(10) Patent No.: US 12,171,613 B2
(45) Date of Patent: Dec. 24, 2024

(54) COMPUTED TOMOGRAPHY (CT) DEVICE WITH ENERGY STORAGE SYSTEM

(71) Applicant: SHANDONG DACHENG MEDICAL TECHNOLOGY CO., LTD., Shandong (CN)

(72) Inventors: Mu Chen, Shandong (CN); Chengfeng Wu, Shandong (CN); Meiling Wang, Shandong (CN); Mingxiu Zhu, Shandong (CN); Deli Lu, Shandong (CN)

(73) Assignee: SHANDONG DACHENG MEDICAL TECHNOLOGY CO., LTD., Shandong (CN)

( * ) Notice: Subject to any disclaimer, the term of this patent is extended or adjusted under 35 U.S.C. 154(b) by 182 days.

(21) Appl. No.: 17/626,785

(22) PCT Filed: Jul. 1, 2020

(86) PCT No.: PCT/CN2020/099740
§ 371 (c)(1),
(2) Date: Jan. 12, 2022

(87) PCT Pub. No.: WO2021/008369
PCT Pub. Date: Jan. 21, 2021

(65) Prior Publication Data
US 2022/0249051 A1 Aug. 11, 2022

(30) Foreign Application Priority Data

Jul. 12, 2019 (CN) .......................... 201910629822.9

(51) Int. Cl.
A61B 6/00 (2024.01)
A61B 6/03 (2006.01)
(Continued)

(52) U.S. Cl.
CPC ................ A61B 6/56 (2013.01); A61B 6/035 (2013.01); A61B 6/0407 (2013.01);
(Continued)

(58) Field of Classification Search
None
See application file for complete search history.

(56) References Cited

U.S. PATENT DOCUMENTS 5,023,768 A  6/1991 Collier
5,226,064 A * 7/1993 Yahata ..................... H05G 1/26
378/102
(Continued)

FOREIGN PATENT DOCUMENTS

CN  1575759 A  2/2005
CN  102047359 A  5/2011
(Continued)

Primary Examiner — David P Porta
Assistant Examiner — Djura Malevic
(74) Attorney, Agent, or Firm — Bayramoglu Law Offices LLC

(57) ABSTRACT

A computed tomography (CT) device with an energy storage system includes an energy storage system, a scanning gantry, a diagnostic couch and a console. The energy storage system is respectively connected to the scanning gantry, the diagnostic couch and the console, and can supply power for the scanning gantry, the diagnostic couch and the console. The energy storage system comprises a charging part, an energy storage module and an output part. The scanning gantry comprises a rotor portion and a stator portion. The CT device uses the energy storage system to supply power to the whole CT device, uses a direct current (DC)-alternating current (AC) inverter to convert a DC of the energy storage system into an AC for power supply, and uses a DC-DC converter to convert a voltage of the energy storage system into different voltages for power supply.

7 Claims, 2 Drawing Sheets

(51) Int. Cl.
A61B 6/04 (2006.01)
H01R 39/08 (2006.01)
(52) U.S. Cl.
CPC .............. A61B 6/4435 (2013.01); A61B 6/54 (2013.01); H01R 39/08 (2013.01)

(56) References Cited

U.S. PATENT DOCUMENTS

| | | | | |
|---|---|---|---|---|
| 5,608,771 | A | 3/1997 | Steigerwald et al. | |
| 5,808,376 | A * | 9/1998 | Gordon | H02J 1/02 307/64 |
| 6,671,345 | B2 * | 12/2003 | Vrettos | A61B 6/4233 378/19 |
| 6,674,836 | B2 * | 1/2004 | Harada | H05G 1/10 378/107 |
| 6,975,698 | B2 * | 12/2005 | Katcha | A61B 6/56 378/107 |
| 7,054,411 | B2 * | 5/2006 | Katcha | A61B 6/56 378/101 |
| 7,110,488 | B2 * | 9/2006 | Katcha | A61B 6/56 378/107 |
| 7,197,113 | B1 * | 3/2007 | Katcha | A61B 6/032 378/104 |
| 7,397,896 | B2 * | 7/2008 | Beyerlein | H05G 1/10 378/111 |
| 7,447,293 | B2 * | 11/2008 | Kasuya | G01N 23/046 378/103 |
| 7,668,295 | B2 * | 2/2010 | Tang | H05G 1/54 378/101 |
| 7,684,538 | B2 * | 3/2010 | Morton | A61B 6/4028 378/10 |
| 7,755,055 | B2 * | 7/2010 | Schilling | A61B 6/56 250/370.09 |
| 7,929,663 | B2 * | 4/2011 | Morton | G01F 1/74 378/53 |
| 7,932,693 | B2 * | 4/2011 | Lee | H02M 7/53875 318/727 |
| 8,041,002 | B2 * | 10/2011 | Gatten | G01V 5/226 378/207 |
| 8,076,943 | B2 * | 12/2011 | Brach | G01R 31/086 324/536 |
| 8,135,110 | B2 * | 3/2012 | Morton | G01V 5/22 378/57 |
| 8,164,929 | B2 * | 4/2012 | Zimpfer | H02M 7/64 378/4 |
| 8,194,818 | B2 * | 6/2012 | Meng | A61B 6/56 378/204 |
| 8,218,726 | B2 * | 7/2012 | Bressel | A61B 6/56 378/103 |
| 8,223,919 | B2 * | 7/2012 | Morton | H01J 35/045 378/57 |
| 8,451,974 | B2 * | 5/2013 | Morton | G01V 5/226 378/57 |
| 8,519,721 | B2 * | 8/2013 | Krumme | H02J 50/50 378/101 |
| 8,563,941 | B1 * | 10/2013 | Chappo | G01T 1/2006 250/370.11 |
| 8,581,437 | B2 * | 11/2013 | Delforge | H02M 7/53871 307/11 |
| 8,670,272 | B2 * | 3/2014 | Radke | G11C 29/50 365/201 |
| 8,696,201 | B2 * | 4/2014 | Kraft | G01T 7/005 378/207 |
| 8,804,899 | B2 * | 8/2014 | Morton | G01T 1/17 378/19 |
| 8,861,678 | B2 * | 10/2014 | Liu | H05G 1/08 378/91 |
| 8,861,681 | B2 * | 10/2014 | Caiafa | H05G 1/10 378/111 |
| 8,885,794 | B2 * | 11/2014 | Morton | G21K 1/025 378/57 |
| 8,891,733 | B2 * | 11/2014 | Liu | A61B 6/56 378/91 |
| 9,008,275 | B2 * | 4/2015 | Hanlon | H05G 1/58 378/104 |
| 9,048,061 | B2 * | 6/2015 | Morton | G01V 5/00 |
| 9,084,335 | B2 * | 7/2015 | Mekonnen | A61B 6/035 |
| 9,113,839 | B2 * | 8/2015 | Morton | A61B 6/4028 |
| 9,138,195 | B2 * | 9/2015 | Krupica | H01Q 1/38 |
| 9,154,014 | B2 * | 10/2015 | Kalenyak | F16C 32/04 |
| 9,183,647 | B2 * | 11/2015 | Morton | A61B 6/542 |
| 9,186,120 | B2 * | 11/2015 | Zimpfer | A61B 6/56 |
| 9,205,281 | B2 * | 12/2015 | Mazin | A61N 5/1081 |
| 9,223,050 | B2 * | 12/2015 | Kaval | G01N 23/04 |
| 9,285,498 | B2 * | 3/2016 | Carver | G01N 23/04 |
| 9,332,624 | B2 * | 5/2016 | Morton | G01V 5/20 |
| 9,364,187 | B2 * | 6/2016 | Lacey | G01T 1/243 |
| 9,429,530 | B2 * | 8/2016 | Morton | G01N 23/201 |
| 9,438,120 | B2 * | 9/2016 | Caiafa | H05G 1/58 |
| 9,649,085 | B2 * | 5/2017 | Herrmann | H02H 7/125 |
| 9,675,306 | B2 * | 6/2017 | Morton | A61B 6/487 |
| 9,722,429 | B2 * | 8/2017 | Weedon | A61B 6/56 |
| 9,747,705 | B2 * | 8/2017 | Morton | A61B 6/542 |
| 9,791,590 | B2 * | 10/2017 | Morton | G01V 5/232 |
| 10,024,935 | B2 * | 7/2018 | Ham | G01R 33/3852 |
| 10,048,337 | B2 * | 8/2018 | Yokoi | G01R 33/36 |
| 10,050,471 | B2 * | 8/2018 | Krumme | A61B 6/03 |
| 10,098,214 | B2 * | 10/2018 | Morton | G01V 5/20 |
| 10,175,381 | B2 * | 1/2019 | Morton | H05G 1/70 |
| 10,251,252 | B2 * | 4/2019 | Kim | H02J 50/10 |
| 10,295,483 | B2 * | 5/2019 | Morton | G01T 1/2985 |
| 10,317,566 | B2 * | 6/2019 | Morton | G01N 23/083 |
| 10,327,716 | B2 * | 6/2019 | Mazin | A61B 6/037 |
| 10,342,506 | B2 * | 7/2019 | Beyerlein | A61B 6/542 |
| 10,349,505 | B2 * | 7/2019 | Heidrich | H01J 35/16 |
| 10,478,133 | B2 * | 11/2019 | Levy | A61B 6/585 |
| 10,488,532 | B2 * | 11/2019 | Abenaim | G01T 1/20184 |
| 10,585,207 | B2 * | 3/2020 | Morton | G01V 5/271 |
| 10,591,424 | B2 * | 3/2020 | Morton | H01J 35/04 |
| 10,620,281 | B2 * | 4/2020 | Kanakasabai | H02J 7/34 |
| 10,646,192 | B2 * | 5/2020 | Shanthakumar | A61B 6/032 |
| 10,652,988 | B2 * | 5/2020 | Kim | A61B 6/4452 |
| 10,670,769 | B2 * | 6/2020 | Morton | G01V 5/232 |
| 10,695,586 | B2 * | 6/2020 | Harper | A61N 5/1081 |
| 10,728,995 | B2 * | 7/2020 | Kim | H02J 7/00309 |
| 10,976,271 | B2 * | 4/2021 | Morton | G06T 7/12 |
| 11,550,077 | B2 * | 1/2023 | Morton | G01V 5/22 |
| 11,558,082 | B2 * | 1/2023 | Del Antonio | H04B 5/72 |
| 11,559,270 | B2 * | 1/2023 | Gregerson | H05G 1/10 |
| 11,594,001 | B2 * | 2/2023 | Sivakumar | G06F 3/165 |
| 11,596,808 | B2 * | 3/2023 | Maltz | A61B 6/102 |
| 11,611,230 | B2 * | 3/2023 | Biber | G01R 33/3815 |
| 11,726,220 | B2 * | 8/2023 | Marsden | G01T 1/2018 378/4 |
| 2004/0022351 | A1 * | 2/2004 | Lacey | A61B 6/4488 378/19 |
| 2004/0071259 | A1 * | 4/2004 | Lacey | A61B 6/035 378/19 |
| 2004/0264642 | A1 * | 12/2004 | Katcha | A61B 6/56 378/107 |
| 2005/0226380 | A1 * | 10/2005 | Katcha | A61B 6/56 378/101 |
| 2005/0243964 | A1 * | 11/2005 | Katcha | H05G 1/10 378/15 |
| 2005/0281377 | A1 * | 12/2005 | Heinze | H05G 1/10 378/101 |
| 2005/0287008 | A1 * | 12/2005 | Lacey | A61B 6/4488 417/44.1 |
| 2006/0239397 | A1 | 10/2006 | Kobayashi et al. | |
| 2007/0253540 | A1 * | 11/2007 | Anderton | A61B 6/4411 378/198 |
| 2008/0069296 | A1 * | 3/2008 | Joshi | A61B 6/032 250/370.11 |
| 2008/0112537 | A1 * | 5/2008 | Katcha | A61B 6/032 378/102 |
| 2009/0095926 | A1 * | 4/2009 | MacNeish, III | H01J 31/49 250/505.1 |
| 2009/0257548 | A1 * | 10/2009 | Joshi | A61B 6/035 378/4 |

(56) References Cited

U.S. PATENT DOCUMENTS

| | | | |
|---|---|---|---|
| 2010/0220837 A1* | 9/2010 | Bressel | A61B 6/56 378/103 |
| 2011/0019797 A1* | 1/2011 | Morton | G01N 24/084 378/57 |
| 2011/0291108 A1* | 12/2011 | Shen | H01L 31/107 257/77 |
| 2011/0302432 A1* | 12/2011 | Harris | H02J 7/345 320/167 |
| 2012/0219116 A1* | 8/2012 | Thompson | H05G 1/52 378/62 |
| 2012/0256099 A1* | 10/2012 | Gregerson | A61B 6/035 378/4 |
| 2013/0336447 A1* | 12/2013 | Morton | G01N 23/203 378/57 |
| 2014/0070812 A1* | 3/2014 | Yokoi | A61B 6/56 324/322 |
| 2014/0211916 A1* | 7/2014 | Morton | G01V 5/22 378/57 |
| 2014/0239715 A1* | 8/2014 | Weedon | H01F 38/18 307/17 |
| 2015/0110240 A1* | 4/2015 | Morton | G01N 23/046 378/10 |
| 2015/0319830 A1* | 11/2015 | Lacey | A61B 6/035 378/19 |
| 2015/0342543 A1* | 12/2015 | Khen | G06T 11/005 250/362 |
| 2015/0362440 A1* | 12/2015 | Thompson | G01N 23/04 378/92 |
| 2016/0174920 A1* | 6/2016 | Lacey | A61B 6/4488 378/189 |
| 2016/0181791 A1* | 6/2016 | Herrmann | H05G 1/10 307/104 |
| 2016/0231454 A1* | 8/2016 | Morton | G01N 24/084 |
| 2017/0112454 A1* | 4/2017 | Yun | A61B 6/54 |
| 2018/0038988 A1* | 2/2018 | Morton | G01N 23/046 |
| 2018/0128935 A1* | 5/2018 | Morton | G01V 5/232 |
| 2018/0325477 A1* | 11/2018 | Wang | A61B 6/032 |
| 2019/0336795 A1* | 11/2019 | Zhou | A61N 5/1081 |
| 2020/0074120 A1* | 3/2020 | Meiler | G06F 21/86 |
| 2020/0074123 A1* | 3/2020 | Meiler | G06F 21/71 |
| 2021/0212653 A1* | 7/2021 | Imamura | A61B 6/542 |
| 2022/0249051 A1* | 8/2022 | Chen | A61B 6/032 |
| 2024/0312642 A1* | 9/2024 | Mathur | G16H 80/00 |

FOREIGN PATENT DOCUMENTS

| | | |
|---|---|---|
| CN | 102279643 A | 12/2011 |
| CN | 103997966 A | 8/2014 |
| CN | 105720698 A | 6/2016 |
| CN | 109620279 A | 4/2019 |
| CN | 109646037 A | 4/2019 |
| CN | 110313929 A | 10/2019 |
| CN | 210990354 U | 7/2020 |
| WO | 2015158180 A1 | 10/2015 |

* cited by examiner

COMPUTED TOMOGRAPHY (CT) DEVICE WITH ENERGY STORAGE SYSTEM

CROSS REFERENCE TO THE RELATED APPLICATIONS

This application is the national phase entry of International Application No. PCT/CN2020/099740, filed on Jul. 1, 2020, which is based upon and claims priority to Chinese Patent Application No. 201910629822.9, filed on Jul. 12, 2019, the entire contents of which are incorporated herein by reference.

TECHNICAL FIELD

The present invention relates to the field of medical instruments, and more particularly, to a computed tomography (CT) device with an energy storage system.

BACKGROUND

A CT device needs to be stably powered with high quality power source. The prior CT device is generally powered by an alternating current (AC) of a power grid. In some extreme environments in which no power grid is available or the power grid collapses, the CT device cannot be used because it cannot be powered. In addition, a mobile CT device cannot be used either in some places if there is no satisfactory AC of the power grid. The dependence on the power grid limits application scenarios of the CT device.

The patent document with publication number CN 109646037A discloses a CT instrument including a scanning gantry. The scanning gantry is U-shaped, and includes a base plate, a first mounting plate, and a second mounting plate; a rotating rack, where two ends of the rotating rack are rotatably connected to the first mounting plate and the second mounting plate respectively, and the first mounting plate is provided with a first through hole right against the rotating rack, such that a to-be-scanned object can enter the rotating rack through the first through hole; and a scanning assembly, including an X-ray source and a detector that are disposed on a side wall of the rotating rack. In the aforementioned CT instrument, the U-shaped scanning gantry is used to install the rotating rack, and the two ends of the rotating rack are rotatably connected to the first mounting plate and the second mounting plate respectively, so that during rotation of the rotating rack, the base plate receives a uniform force. When a same stability condition is met, compared with a non-uniform force on a base of an L-shaped scanning gantry, the uniform force reduces a weight requirement for the base plate, thereby reducing the weight of the CT instrument and obtaining a CT instrument with relatively small mass. However, such a CT instrument needs to be powered by the power grid and is inconvenient to move. As a result, the CT instrument is not suitable for special extreme applications, such as a disaster relief site in which the power grid collapses.

SUMMARY

To overcome the shortcomings in the prior art, the present invention is intended to provide a CT device with an energy storage system.

A CT device with an energy storage system provided in the present invention includes an energy storage system, a scanning gantry, a diagnostic couch and a console.

The energy storage system is respectively connected to the scanning gantry, the diagnostic couch and the console, and can supply power for the scanning gantry, the diagnostic couch and the console.

Preferably, the energy storage system includes a charging part, an energy storage module and an output part, the charging part is connected to the energy storage module, and the energy storage module is connected to the output part.

Preferably, the charging part is connected to a charging device or a power supply network through a charging interface to charge the energy storage module.

The charging interface includes a direct current (DC) charging interface and/or an AC charging interface.

The energy storage module includes one or more super-capacitor modules.

Preferably, the output part includes at least one high-voltage output channel and at least one low-voltage output channel.

Preferably, a DC voltage output by the high-voltage output channel ranges from 455 V to 620 V, and a DC voltage output by the low-voltage output channel ranges from 90 V to 135 V.

Preferably, the scanning gantry includes a rotor portion and a stator portion.

The rotor portion includes a slip ring, a high-voltage generator, an X-ray tube, a rotor portion DC-DC converter, a rotor portion control board, a CT detector, a rotor portion DC-AC inverter and a heat exchange apparatus. The rotor portion control board is respectively connected to the high-voltage generator, the X-ray tube, the CT detector and the heat exchange apparatus.

A high-voltage rail input end of the slip ring is connected to a high-voltage output channel of an output part of the energy storage system, a high-voltage rail output end of the slip ring is connected to an input end of the high-voltage generator, and an output end of the high-voltage generator is connected to an input end of the X-ray tube. A low-voltage rail input end of the slip ring is connected to a low-voltage output channel of the output part of the energy storage system, a low-voltage rail output end of the slip ring is respectively connected to an input end of the rotor portion DC-DC converter and an input end of the rotor portion DC-AC inverter, an output end of the rotor portion DC-DC converter is respectively connected to the rotor portion control board and the CT detector, and an output end of the rotor portion DC-AC inverter is connected to the heat exchange apparatus.

The stator portion includes a rotating driver, a rotating motor, a stator portion DC-DC converter and a stator portion control board. The rotating motor drives the rotor portion to rotate. The stator portion control board is connected to the rotating driver.

An input end of the rotating driver is connected to the high-voltage output channel of the output part of the energy storage system, and an output end of the rotating driver is connected to the rotating motor. An input end of the stator portion DC-DC converter is connected to the low-voltage output channel of the output part of the energy storage system, and an output end of the stator portion DC-DC converter is connected to the stator portion control board.

Preferably, the slip ring includes one or more conductive rails, each conductive rail is an annular broad-stripe copper bar, each conductive rail can separately transfer a power supply, and the conductive rails are disposed on the rotor portion.

The slip ring further includes one or more conductive brushes, the conductive brushes are connected to the output part of the energy storage system, the conductive brushes are connected to the conductive rails in one-to-one correspondence to realize conduction, and the conductive brushes are disposed on the stator portion.

Preferably, the diagnostic couch includes a diagnostic couch DC-AC inverter, a vertical driver, and a horizontal driver, an input end of the diagnostic couch DC-AC inverter is connected to a low-voltage output channel of an output part of the energy storage system, and an output end of the diagnostic couch DC-AC inverter is respectively connected to the vertical driver and the horizontal driver.

The vertical driver drives the diagnostic couch to move vertically, and the horizontal driver drives the diagnostic couch to move horizontally.

Preferably, the console includes a console DC-AC inverter and a main control computer, an input end of the console DC-AC inverter is connected to a low-voltage output channel of an output part of the energy storage system, and an output end of the console DC-AC inverter is connected to the main control computer.

Preferably, each two of the rotor portion control board, the stator portion control board, and the console are connected through a signal.

Compared with the prior art, the present invention has the following beneficial effects.

1. The present invention uses the energy storage system to supply power to the whole CT device, without reducing or degrading performance of the CT device, to resolve a problem that a traditional CT device can only be installed in a fixed place because it is powered by the power supply network. The CT device provided in the present invention can be mobile and is suitable for disaster relief scenes, and can also be mounted on a vehicle, such that the CT device can be used conveniently in more scenarios.

2. The present invention uses the DC-AC inverter to convert a DC of the energy storage system into an AC for power supply, to resolve a problem that some components of the CT device cannot be directly powered by a DC power supply.

3. The present invention uses the DC-DC converter to convert a voltage of the energy storage system into different voltages for power supply, to resolve a problem that some components of the CT device need to be powered by a safe low-voltage DC power supply.

BRIEF DESCRIPTION OF THE DRAWINGS

Other features, objectives, and advantages of the present invention will become more apparent by reading the detailed description of non-limiting embodiments with reference to the following accompanying drawings.

REFERENCE NUMERALS

Figure 1:
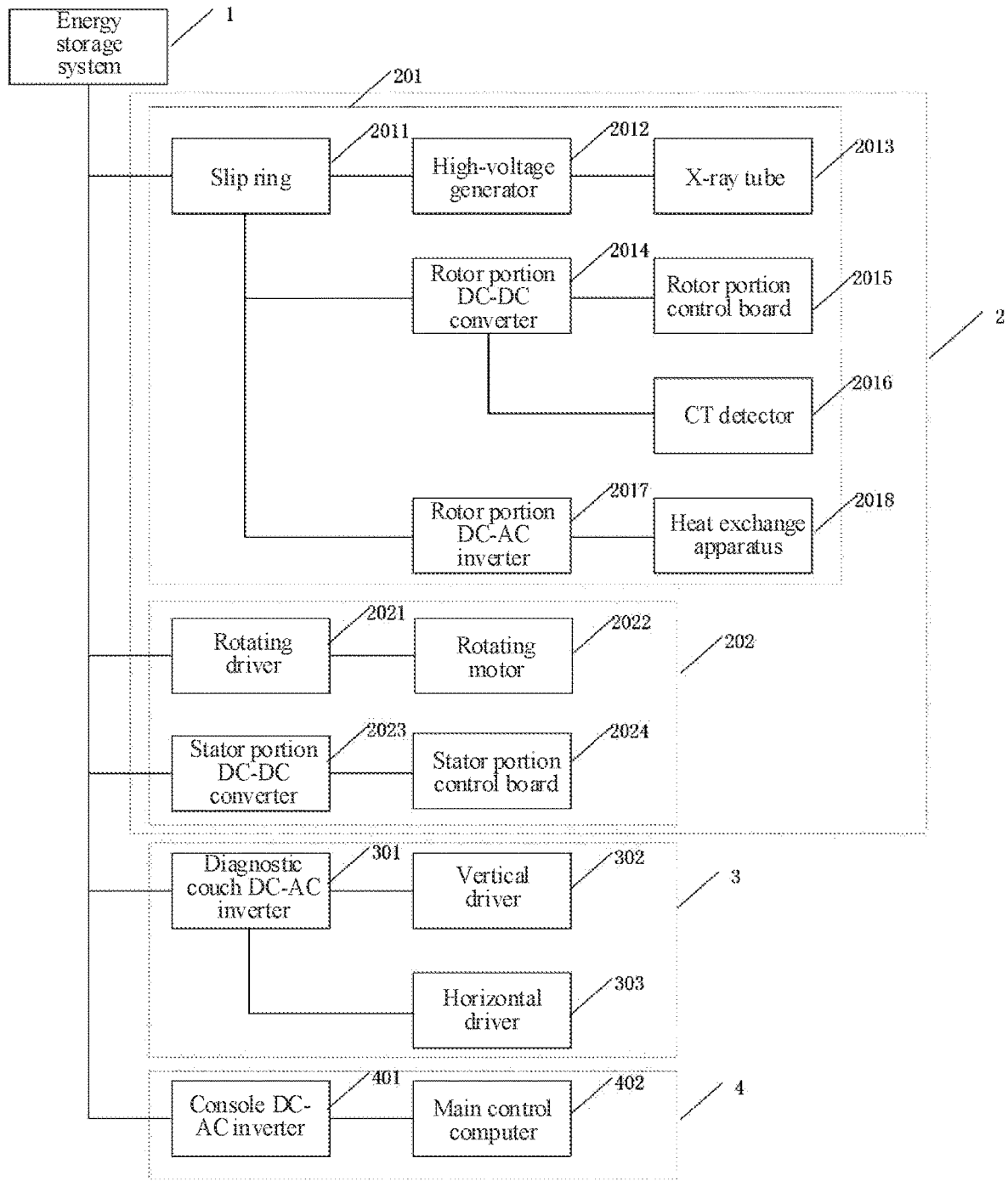
FIG. 1 is a schematic block diagram of power supply according to the present invention.

| Energy storage system 1 | CT detector 2016 | Diagnostic couch 3 |
|---|---|---|
| Scanning gantry 2 | Rotor portion DC-AC inverter 2017 | Diagnostic couch DC-AC inverter 301 |
| Rotor portion 201 | Heat exchange apparatus 2018 | vertical driver 302 |
| Slip ring 2011 | Stator portion 202 | horizontal driver 303 |
| High-voltage generator 2012 | rotating driver 2021 | Console 4 |
| X-ray tube 2013 | Rotating motor 2022 | Console DC-AC inverter 401 |
| Rotor portion DC-DC converter 2014 | Stator portion DC-DC converter 2023 | Main control computer 402 |
| Rotor portion control board 2015 | Stator portion control board 2024 | |

DETAILED DESCRIPTION OF THE EMBODIMENTS

The present invention is described in detail below with reference to specific embodiments. The following embodiments will help those skilled in the art to further understand the present invention, but do not limit the present invention in any way. It should be noted that several variations and improvements can also be made by a person of ordinary skill in the art without departing from the conception of the present invention. These all fall within the protection scope of the present invention.

The present invention uses an energy storage system to supply power to a whole CT device, such that the CT device can work when there is no power supply network, thereby expanding application scenarios of the CT device and promoting the development of mobile medical devices. An energy storage system 1 provides a DC power supply for a scanning gantry 2, a diagnostic couch 3, and a console 4. Among the power-driven components of the scanning gantry 2, the diagnostic couch 3, and the console 4, some support DC high-voltage power supply, some support DC low-voltage power supply, and some support AC power supply. The components supporting DC high-voltage power supply are powered by using a high-voltage output channel of the energy storage system 1. The components supporting DC low-voltage power supply are powered after a DC-DC converter reduces a voltage output by a low-voltage output channel of the energy storage system 1. The DC-DC converter can not only reduce the voltage, but also increase the voltage. The components supporting AC power supply are powered after a DC-AC inverter converts a DC voltage output by the low-voltage channel of the energy storage system 1 into an AC voltage. The DC-AC inverter can not only convert a DC into an AC, but also can change the output voltage. The present invention uses the energy storage system to supply power to the whole CT device, and performance of the CT device is not reduced or degraded. On the contrary, some individual indexes are higher than those achieved when the CT device is powered by a traditional power supply network of a same level.

Figure 2:
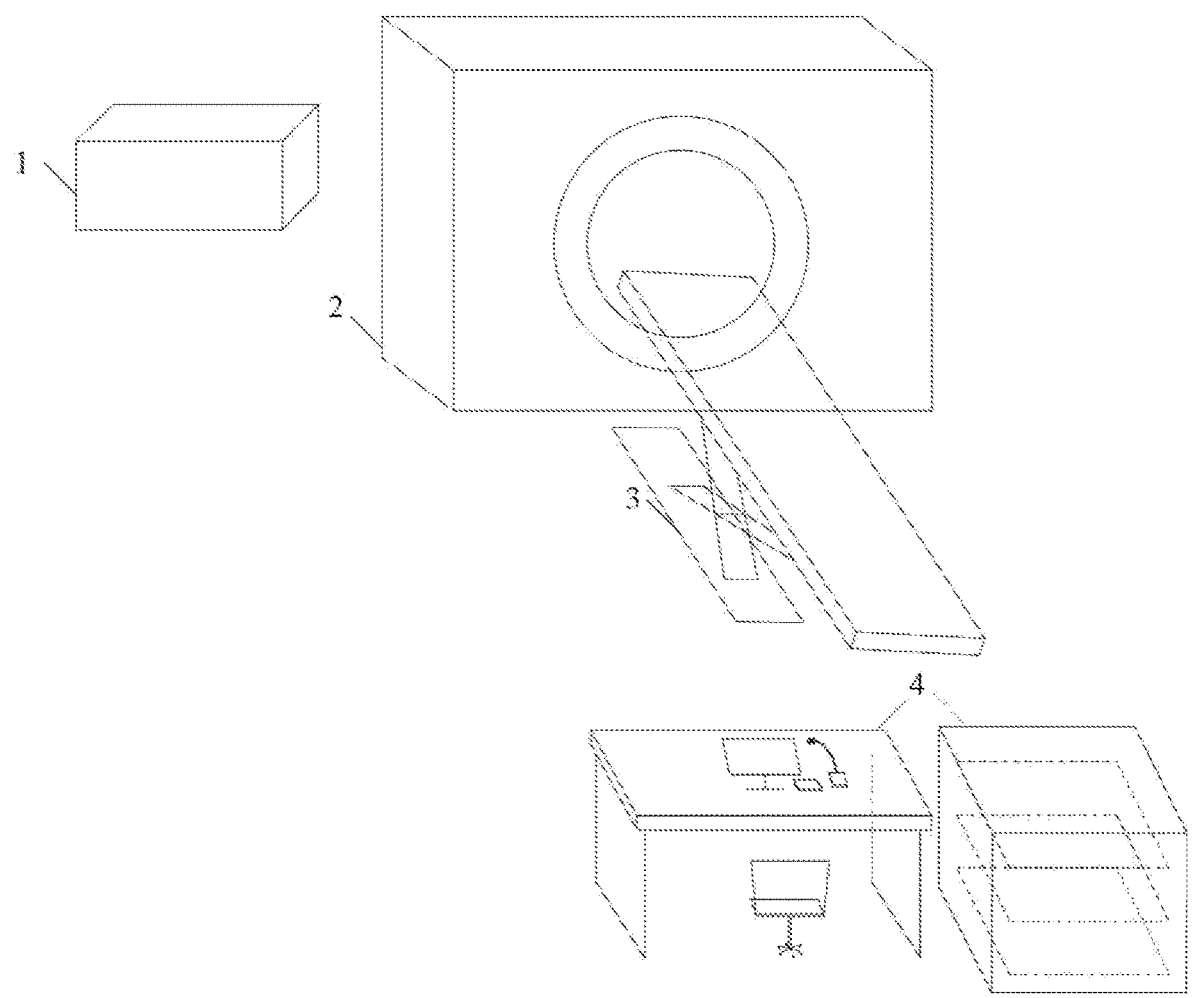
FIG. 2 is a schematic structural diagram of the present invention.

As shown in FIG. 1 and FIG. 2, a CT device with an energy storage system provided in the present invention includes an energy storage system 1, a scanning gantry 2, a diagnostic couch 3, and a console 4. The energy storage system 1 is respectively connected to the scanning gantry 2, the diagnostic couch 3 and the console 4, and can supply power for the scanning gantry 2, the diagnostic couch 3 and the console 4. The energy storage system 1 is a new energy storage system, which is a power source storage system made of new energy, new materials, composite materials or environmental protection materials. The connections described herein are all electrical connections.

The energy storage system 1 includes a charging part, an energy storage module and an output part, the charging part is connected to the energy storage module, and the energy storage module is connected to the output part. The charging part is connected to a charging device or a power supply network through a charging interface to charge the energy storage module, or charges the energy storage module by using solar energy. The charging interface includes a DC charging interface and/or an AC charging interface. The energy storage module includes one or more supercapacitor modules. The energy storage system 1 can be charged and discharged simultaneously. The output part includes at least one high-voltage output channel and at least one low-voltage output channel. A DC voltage output by the high-voltage output channel ranges from 455 V to 620 V, and a DC voltage output by the low-voltage output channel ranges from 90 V to 135 V. The energy storage system 1 further includes a power management part. The power management part monitors a temperature, a voltage, a current, and an electric quantity of the energy storage module, and can report an alarm for an abnormality. The output part includes an output control board. The output control board is configured to perform power-on and power-off timing control by driving a DC contactor of the output channel, and set a cut-off voltage for each output channel. When a voltage of each output channel is higher than the cut-off voltage, the energy storage system 1 is discharging. When the voltage of each output channel is lower than the cut-off voltage, the energy storage system 1 is charging and reports an alarm automatically.

The scanning gantry 2 includes a rotor portion 201 and a stator portion 202. The rotor portion includes a slip ring 2011, a high-voltage generator 2012, an X-ray tube 2013, a rotor portion DC-DC converter 2014, a rotor portion control board 2015, a CT detector 2016, a rotor portion DC-AC inverter 2017 and a heat exchange apparatus 2018. The rotor portion control board 2015 is respectively connected to the high-voltage generator 2012, the X-ray tube 2013, the CT detector 2016 and the heat exchange apparatus 2018. A high-voltage rail input end of the slip ring 2011 is connected to a high-voltage output channel of an output part of the energy storage system 1, a high-voltage rail output end of the slip ring 2011 is connected to an input end of the high-voltage generator 2012, and an output end of the high-voltage generator 2012 is connected to an input end of the X-ray tube 2013. A low-voltage rail input end of the slip ring 2011 is connected to a low-voltage output channel of the output part of the energy storage system 1, a low-voltage rail output end of the slip ring 2011 is respectively connected to an input end of the rotor portion DC-DC converter 2014 and an input end of the rotor portion DC-AC inverter 2017, an output end of the rotor portion DC-DC converter 2014 is respectively connected to the rotor portion control board 2015 and the CT detector 2016, and an output end of the rotor portion DC-AC inverter 2017 is connected to the heat exchange apparatus 2018.

The stator portion 202 includes a rotating driver 2021, a rotating motor 2022, a stator portion DC-DC converter 2023 and a stator portion control board 2024. The rotating motor 2022 drives the rotor portion 201 to rotate, and the stator portion control board 2024 is connected to the rotating driver 2021. An input end of the rotating driver 2021 is connected to the high-voltage output channel of the output part of the energy storage system 1, and an output end of the rotating driver 2021 is connected to the rotating motor 2022. An input end of the stator portion DC-DC converter 2023 is connected to the low-voltage output channel of the output part of the energy storage system 1, and an output end of the stator portion DC-DC converter 2023 is connected to the stator portion control board 2024. The rotating driver 2021 can be directly powered by a high-voltage output power supply of the energy storage system 1. The rotating driver 2021 is configured to provide a sufficient dynamic power supply for the rotating motor 2022 and realize motion control for the rotating motor 2022. The rotating motor 2022 is configured to drag a belt to drive a bearing to enable the rotor portion 201 to rotate. The stator portion DC-DC converter 2023 is configured to convert a low-voltage DC output by the energy storage system 1 into a lower DC voltage. In an embodiment, a 90 V to 135 V DC voltage is converted into a 24 V DC voltage to supply power for the stator portion control board 2024. As a central control board of the entire system, the stator portion control board 2024 is configured to send an instruction to the rotating driver 2021 or receive a signal from the rotating driver 2021, perform signal transmission with the rotor portion control board 2015, and communicate with the console 4.

The slip ring 2011 includes one or more conductive rails, each conductive rail is an annular broad-stripe copper bar, each conductive rail can separately transfer a power supply, and the conductive rails are disposed on the rotor portion 201. The slip ring 2011 further includes one or more conductive brushes, the conductive brushes are connected to the output part of the energy storage system 1, the conductive brushes are connected to the conductive rails in one-to-one correspondence to realize conduction, and the conductive brushes are disposed on the stator portion 202. Preferably, the conductive brush is a carbon brush.

A power supply of the rotor portion 201 is transferred from the energy storage system 1 to the rotor portion 201 through the slip ring 2011. The slip ring 2011 is a conductive component connecting the stator portion 202 and the rotor portion 201. The slip ring 2011 is a structure that is composed of an annular broad-stripe copper bar and a carbon brush and that is used to replace a cable. A plurality of rails can be used to transfer a plurality of independent power supplies. The bearing installed on the slip ring 2011 is dragged by the belt of the rotating motor 2022 to perform continuous unidirectional rotation. The carbon brush is fixed on the stator portion. The rotor portion 201 and the stator portion 202 are conducted between the conductive rail and the carbon brush of the slip ring 2011, such that the CT device can perform spiral scanning at a high speed without a power failure. A high-voltage power supply output by the energy storage system 1 is connected to a head of a carbon brush corresponding to a high-voltage rail of the slip ring 2011 by using a power cable, and then connected to an input end of a main power supply of the high-voltage generator 2012 by using a power cable through an output end of a high-voltage rail on a rear side of the slip ring 2011, to drive the high-voltage generator 2012 to provide the X-ray tube 2013 with a stable DC high voltage with sufficient power and obtained after high frequency inversion, and to provide a voltage for a driving circuit of a rotating anode. A filament current control circuit is provided for a filament of the X-ray tube 2013 to generate a stable tube current. The X-ray tube 2013 is configured to perform X-ray emission and temperature control. The rotor portion DC-DC converter 2014 is configured to perform voltage reduction on a low-voltage DC power supply transferred from the energy storage system 1 to the rotor portion 201 through the slip ring 2011. In an embodiment, the 90 V to 135 V DC voltage is converted into the 24 V DC voltage to supply power for the rotor portion control board 2015 and CT detector 2016. The rotor portion control board 2015 is configured to control X-ray scanning, data generation and transmission, abnormality reporting, and other processing. The CT detector 2016 is configured to convert X-ray energy into an electrical signal. Therefore, the CT detector 2016 is opposite to the X-ray tube 2013. In addition, the CT detector 2016 is disposed in an arc shape to form a sector region with the X-ray tube 2013, such that X-rays are mapped onto the CT detector 2016. The rotor portion DC-AC inverter 2017 is configured to invert the low-voltage DC power supply transferred from the energy storage system 1 to the rotor portion 201 through the slip ring 2011. In an embodiment, the 90 V to 135 V DC voltage is inverted into a 220 V AC voltage to supply power required by the heat exchange apparatus 2018. The heat exchanger apparatus 2018 performs heat dissipation for the X-ray tube 2013 through oil circulation and air cooling.

The diagnostic couch 3 includes a diagnostic couch DC-AC inverter 301, a vertical driver 302, and a horizontal driver 303. An input end of the diagnostic couch DC-AC inverter 301 is connected to the low-voltage output channel of the output part of the energy storage system 1, and an output end of the diagnostic couch DC-AC inverter 301 is respectively connected to the vertical driver 302 and the horizontal driver 303. The vertical driver 302 drives the diagnostic couch 3 to move vertically, and the horizontal driver 303 drives the diagnostic couch 3 to move horizontally. The diagnostic couch DC-AC inverter 301 is configured to invert the low-voltage DC power supply provided by the energy storage system 1 into an AC power supply. In an embodiment, the 90 V to 135 V DC voltage is inverted into the 220 V AC voltage. The diagnostic couch 3 has a maximum load of 250 kg.

The console 4 includes a console DC-AC inverter 401 and a main control computer 402. An input end of the console DC-AC inverter 401 is connected to the low-voltage output channel of the output part of the energy storage system 1, and an output end of the console DC-AC inverter 401 is connected to the main control computer 402. The console DC-AC inverter 401 is configured to invert the low-voltage DC power supply provided by the energy storage system into the AC power supply. In an embodiment, a 90 V to 135 V DC power supply is inverted into a 220 V AC power supply that is provided for the main control computer 402. The main control computer 402 is configured to reconstruct, process, and store an image obtained through CT scanning.

Each two of the rotor portion control board 2015, the stator portion control board 2024, and the console 4 are connected through a signal to realize mutual communication and information transmission.

The specific embodiments of the present invention are described above. It should be understood that the present invention is not limited to the above specific implementations, and a person skilled in the art can make various variations or modifications within the scope of the claims without affecting the essence of the present invention. The embodiments in the present invention and features in the embodiments may be arbitrarily combined with each other in a non-conflicting situation.

What is claimed is:

1. A mobile computed tomography (CT) device with an energy storage system, comprising an energy storage system, a scanning gantry, a diagnostic couch and a console, wherein the energy storage system is respectively connected to the scanning gantry, the diagnostic couch and the console, and the energy storage system is configured to supply power for the scanning gantry, the diagnostic couch and the console, the energy storage system being configured to supply power to the whole CT device when the energy storage system and the CT device is disconnected from a power supply network without a reduction or degradation in performance of the CT device, wherein the scanning gantry comprises a rotor portion and a stator portion;

the rotor portion comprises a slip ring, a high-voltage generator, an X-ray tube, a rotor portion DC-DC converter, a rotor portion control board, a CT detector, a rotor portion DC-AC inverter and a heat exchange apparatus; and the rotor portion control board is respectively connected to the high-voltage generator, the X-ray tube, the CT detector and the heat exchange apparatus;

wherein a high-voltage rail input end of the slip ring is connected to a high-voltage output channel of an output part of the energy storage system, a high-voltage rail output end of the slip ring is connected to an input end of the high-voltage generator, and an output end of the high-voltage generator is connected to an input end of the X-ray tube;

wherein a low-voltage rail input end of the slip ring is connected to a low-voltage output channel of the output part of the energy storage system, a low-voltage rail output end of the slip ring is respectively connected to an input end of the rotor portion DC-DC converter and an input end of the rotor portion DC-AC inverter, an output end of the rotor portion DC-DC converter is respectively connected to the rotor portion control board and the CT detector, and an output end of the rotor portion DC-AC inverter is connected to the heat exchange apparatus;

the stator portion comprises a rotating driver, a rotating motor, a stator portion DC-DC converter and a stator portion control board; the rotating motor drives the rotor portion to rotate; and the stator portion control board is connected to the rotating driver;

wherein an input end of the rotating driver is connected to the high-voltage output channel of the output part of the energy storage system, and an output end of the rotating driver is connected to the rotating motor; and an input end of the stator portion DC-DC converter is connected to the low-voltage output channel of the output part of the energy storage system, and an output end of the stator portion DC-DC converter is connected to the stator portion control board, wherein the slip ring comprises one or more conductive rails, wherein each conductive rail of the one or more conductive rails is an annular broad-stripe copper bar, each conductive rail is configured to separately transfer a power supply, and the one or more conductive rails are disposed on the rotor portion; and the slip ring further comprises one or more conductive brushes, wherein the one or more conductive brushes are connected to the output part of the energy storage system, the one or more conductive brushes are connected to the one or more conductive rails in one-to-one correspondence to realize conduction, and the one or more conductive brushes are disposed on the stator portion, wherein each two of the rotor portion control board, the stator portion control board, and the console are connected through a signal.

2. The mobile CT device according to claim 1, wherein the energy storage system comprises a charging part, an energy storage module and an output part, wherein the charging part is connected to the energy storage module, and the energy storage module is connected to the output part.

3. The mobile CT device according to claim 2, wherein the charging part is connected to a charging device or a power supply network through a charging interface to charge the energy storage module;

the charging interface comprises a direct current (DC) charging interface and an alternating current (AC) charging interface; and the energy storage module comprises one or more supercapacitor modules.

4. The mobile CT device according to claim 2, wherein the output part comprises at least one high-voltage output channel and at least one low-voltage output channel.

5. The mobile CT device according to claim 4, wherein a DC voltage output by the high-voltage output channel ranges from 455 V to 620 V, and a DC voltage output by the low-voltage output channel ranges from 90 V to 135 V.

6. The mobile CT device according to claim 1, wherein the diagnostic couch comprises a diagnostic couch DC-AC inverter, a vertical driver, and a horizontal driver, wherein an input end of the diagnostic couch DC-AC inverter is connected to a low-voltage output channel of an output part of the energy storage system, and an output end of the diagnostic couch DC-AC inverter is respectively connected to the vertical driver and the horizontal driver; and the vertical driver drives the diagnostic couch to move vertically, and the horizontal driver drives the diagnostic couch to move horizontally.

7. The mobile CT device according to claim 1, wherein the console comprises a console DC-AC inverter and a main control computer, wherein an input end of the console DC-AC inverter is connected to a low-voltage output channel of an output part of the energy storage system, and an output end of the console DC-AC inverter is connected to the main control computer.

* * * * *